US010780436B2

(12) United States Patent
Liou et al.

(10) Patent No.: US 10,780,436 B2
(45) Date of Patent: Sep. 22, 2020

(54) MULTI-CHANNEL MICROFLUIDIC DEVICE AND METHOD FOR USING THE SAME

(71) Applicant: Advanced NanoBio Technologies Limited, North Point (HK)

(72) Inventors: Yeaun Jau Liou, Sha Tin (HK); Nien-Tsu Huang, North Point (HK)

(73) Assignee: Advanced NanoBio Technologies Limited, North Point (HK)

( * ) Notice: Subject to any disclaimer, the term of this patent is extended or adjusted under 35 U.S.C. 154(b) by 218 days.

(21) Appl. No.: 16/143,108

(22) Filed: Sep. 26, 2018

(65) Prior Publication Data

US 2019/0091684 A1 Mar. 28, 2019

Related U.S. Application Data

(60) Provisional application No. 62/563,438, filed on Sep. 26, 2017.

(51) Int. Cl.

*B01L 3/00* (2006.01)
*C12Q 1/02* (2006.01)
*B01J 19/00* (2006.01)

(52) U.S. Cl.

CPC ... *B01L 3/502715* (2013.01); *B01L 2200/027* (2013.01); *B01L 2200/10* (2013.01); *B01L 2200/141* (2013.01); *B01L 2300/0864* (2013.01); *B01L 2300/0877* (2013.01)

(58) Field of Classification Search

CPC .......... B01L 2200/027; B01L 2200/10; B01L 2200/141; B01L 2300/0864; B01L 2300/0877; B01L 3/502715

See application file for complete search history.

(56) References Cited

U.S. PATENT DOCUMENTS

2012/0164679 A1* 6/2012 Vrouwe ................ C12M 23/12 435/29
2016/0354777 A1* 12/2016 Chiu ......................... B01L 7/52

* cited by examiner

*Primary Examiner* — Jennifer Wecker

(74) *Attorney, Agent, or Firm* — Conley Rose, P.C.; Grant Rodolph

(57) ABSTRACT

A multi-channel microfluidic device for multi-parallel analyte detection includes a substrate and a multi-channel microfluidic assembly formed in the substrate. The multi-channel microfluidic assembly comprises a synchronized port; a plurality of separate ports; a plurality of channels arranged in parallel, where each of the plurality of channels includes a first end and a second end opposite to the first end; a first branch channel assembly; and a plurality of second branch assemblies. The synchronized port is connected with all the first ends of the plurality of the channels via the first branch channel assembly. Each of the plurality of the separate ports is in connection with the second end of each of the plurality of the channels via each of the plurality of the second branch channel assemblies.

18 Claims, 7 Drawing Sheets

FIG. 6A Independent Mode

FIG. 6B Synchronized Mode

FIG. 6C Washing

MULTI-CHANNEL MICROFLUIDIC DEVICE AND METHOD FOR USING THE SAME

CROSS-REFERENCE TO RELATED APPLICATIONS

This application claims priority to U.S. Provisional Application No. 62/563,438 filed on Sep. 26, 2017, the contents of which are incorporated herein by reference in its entirety.

TECHNICAL FIELD

The present application relates to the technical field of microfluidics, and more particularly to a multi-channel microfluidic device for multi-parallel analyte detection and a method for using the same.

BACKGROUND

A microfluidic chip, also known as a lab-on-chip, integrates sample preparation, calibration, and biomarker reaction on a single platform. It only requires a very small volume of sample and reagent, and can realize fast, parallel, and highly sensitive detection of the biochemical reaction. A typical multi-channel microfluidic chip integrates a plurality of independent channels on the chip, with each channel respectively in connection with a plurality of inlets and an outlet, and the valves and pumps are generally arranged on the chip to control the flow path, which results in a complicated structure and a high production cost of the microfluidic chip. Moreover, it is a problem in the microfluidic chip to obtain a uniform injection of the reagents or samples.

SUMMARY

In view of the above-described problems, among others, it is one objective of the present application to provide a multi-channel microfluidic device for multi-parallel analyte detection, which has a different number of ports at two ends thereof and can use both the ports at two ends as inlets to realize a synchronized mode and an independent mode.

It is still another objective of the present application to provide a method for using the multi-channel microfluidic device such that both the ports at two ends can be used as inlets to realize the synchronized mode and the independent mode.

To achieve the above objective, in accordance with one aspect of the present application, there is provided a multi-channel microfluidic device for multi-parallel analyte detection, comprising: a substrate; and a multi-channel microfluidic assembly formed in the substrate. The multi-channel microfluidic assembly comprises: a synchronized port; a plurality of separate ports; a plurality of channels arranged in parallel, each channel of the channels having a first end and a second end opposite to the first end; a first branch channel assembly; and a plurality of second branch assemblies. The synchronized port is coupled with all of the first ends of the channels via the first branch channel assembly, and each of the separate ports is coupled with the second end of each of the channels via each of second branch channel assemblies.

In accordance with another aspect of the present application, there is provided a method for using the above multi-channel microfluidic device. The method comprises: providing a multi-channel microfluidic device; using the synchronized port as an inlet when the channels are to be performed with identical parallel procedures; and using at least a part of the separate ports as separate inlets when at least a part of the channels are to be simultaneously performed with independent procedures. The multi-channel microfluidic device comprises a substrate and a multi-channel microfluidic assembly formed in the substrate. The multi-channel microfluidic assembly comprises: a synchronized port; a plurality of separate ports; a plurality of channels arranged in parallel, each channel of the channels having a first end and a second end opposite to the first end; a first branch channel assembly; and a plurality of second branch assemblies, the synchronized port being coupled with all of the first ends of the channels via the first branch channel assembly, and each of the separate ports being coupled with the second end of each of the channels via each of second branch assembly.

In accordance with still another aspect of the present application, there is provided a microfluidic system for multi-parallel analyte detection comprising a multi-channel microfluidic device. The multi-channel microfluidic device comprises a substrate and a multi-channel microfluidic assembly formed in the substrate. The multi-channel microfluidic assembly comprises: a synchronized port; a plurality of separate ports; a plurality of channels arranged in parallel, each channel of the channels having a first end and a second end opposite to the first end; a first branch channel assembly; and a plurality of second branch assemblies, the synchronized port being coupled with all of the first ends of the channels via the first branch channel assembly, and each of the separate ports being coupled with the second end of each of the channels via each of second branch channel assemblies.

Advantages of the multi-channel microfluidic device and the method for using the same according to embodiments of the present application are summarized as follows:

The multi-channel microfluidic device is provided with one synchronized port and the plurality of the separate ports, and both of the two kinds of ports can be used as inlets to introduce the samples or reagents into the plurality of the channels. In the synchronized mode, the synchronized port is used as the inlet to introduce a certain sample or reagent to the plurality of the channels to perform identical parallel procedures among the plurality of the channels. In the independent mode, the plurality of the separate ports are used as the separate inlets to introduce different samples or reagents to the channels simultaneously, and because different samples or reagents are introduced independently into the channels, cross-contamination issues are avoided. In addition, compared with the conventional multi-channel microfluidic chip integrated thereon with the valves and pumps, the multi-channel microfluidic device according to embodiments of the present application is not required to integrate with the valves or pumps on the chip, thus the structure is much simpler, and combined with an external flow path control system, fluids can be injected from two different directions. Moreover, due to the first branch channel assembly being connected between the synchronized port and all the first ends of the plurality of the channels and the second branch channel assembly being connected between each separate port and the second end of each said channel, the fluid pattern injected into the channels are smooth and uniform.

BRIEF DESCRIPTION OF THE DRAWINGS

The disclosure is described herein below with reference to the accompanying drawings, in which.

Figure 1:
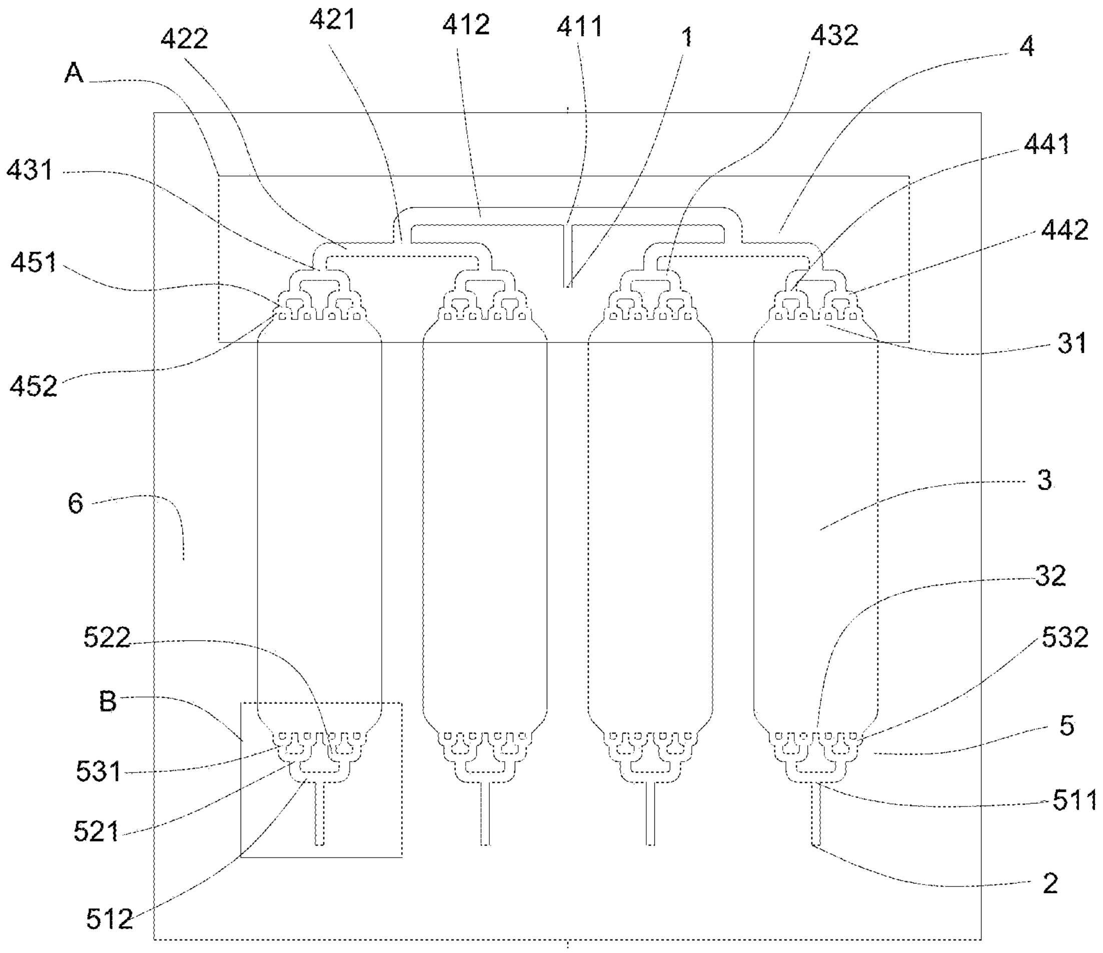
FIG. 1 is a schematic structural diagram of a multi-channel microfluidic device for multi-parallel analyte detection according to an embodiment of the present application.

In the drawings, the following reference numbers are used:

1: Synchronized port; 2: Separate port; 3: Channel; 31: First end of channel; 32: Second end of channel; 4: First branch channel assembly; 411: Primary junction of first branch channel assembly; 412: Primary branch channel of first branch channel assembly; 421: Secondary junction of first branch channel assembly; 422: Secondary branch channel of first branch channel assembly; 431: Tertiary junction of first branch channel assembly; 432: Tertiary branch channel of first branch channel assembly; 441: Quaternary junction of first branch channel assembly; 442: Quaternary branch channel of first branch channel assembly; 451: Quinary junction of first branch channel assembly; 452: Quinary branch channel of first branch channel assembly; 5: Second branch assembly; 511: Primary junction of second branch channel assembly; 512: Primary branch channel of second branch channel assembly; 521: Secondary junction of second branch channel assembly; 522: Secondary branch channel of second branch channel assembly; 531: Tertiary junction of second branch channel assembly; 532: Tertiary branch channel of second branch channel assembly; and 6. Substrate.

DETAILED DESCRIPTION OF THE ENABLING EMBODIMENTS

For further illustrating the disclosure, experiments detailing a multi-channel microfluidic device for multi-parallel analyte detection, and a method for using the multi-channel microfluidic device are described below. It should be noted that the following examples are intended to describe and not to limit the disclosure.

Example 1 Multi-Channel Microfluidic Device

Figure 2:
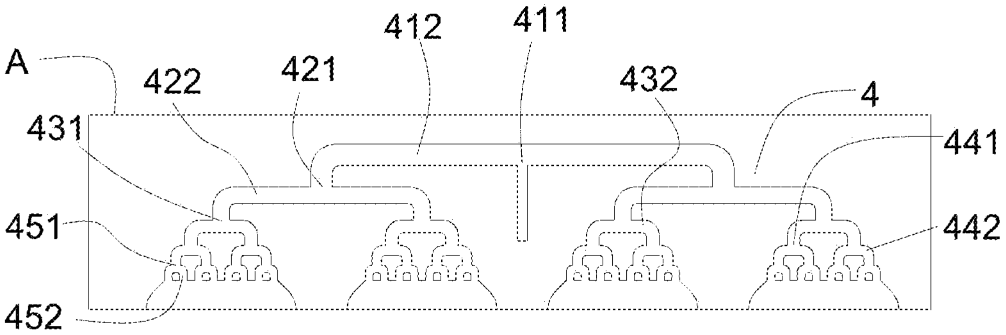
FIG. 2 is an enlarged view taken from part A of FIG. 1.
Figure 3:
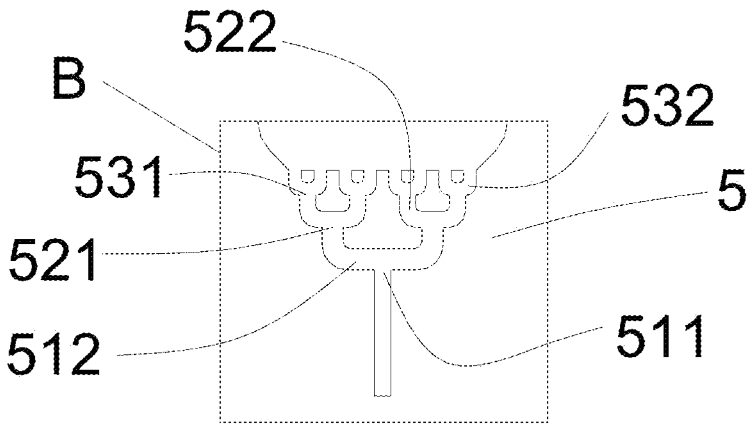
FIG. 3 is an enlarged view taken from part B of FIG. 2.

As shown in FIGS. 1-3, in one aspect of the present application, there is provided a multi-channel microfluidic device for multi-parallel analyte detection, the device comprising a substrate 6 and a multi-channel microfluidic assembly formed in the substrate 6, and the multi-channel microfluidic assembly comprises a synchronized port 1; a plurality of separate ports 2; a plurality of channels 3 arranged in parallel, and each of the plurality of the channels 3 having a first end 31 and a second end 32 opposite to the first end; a first branch channel assembly 4; and a plurality of second branch assemblies 5. The synchronized port 1 is in connection with all of the first ends 31 of the plurality of the channels 3 via the first branch channel assembly 4. Each of the plurality of the separate ports 2 is in connection with the second end 32 of each of the plurality of the channels 3 via each of the plurality of the second branch channel assemblies 5.

The multi-channel microfluidic device is provided with one synchronized port 1 and a plurality of the separate ports 2, both of the two kinds of ports can be used as inlets to introduce the samples or reagents into the channels 3. In a synchronized mode, the synchronized port 1 is used as the inlet to introduce a certain sample or reagent to the plurality of the channels 3 to perform identical parallel procedures among the plurality of the channels 3. In an independent mode, the plurality of the separate ports 2 are used as the separate inlets to introduce different samples or reagents to the channels 3 simultaneously, and because different samples or reagents are introduced independently into the channels 3, cross-contamination issues are avoided. In addition, compared with the conventional multi-channel microfluidic chip integrated thereon with the valves and pumps, the multi-channel microfluidic device as disclosed herein is not required to integrate with the valves or pumps on the chip, thus the structure is much simpler, and combined with an external flow path control system, fluids can be injected from two different directions. Moreover, due to the first branch channel assembly being connected between the synchronized port and all the first ends of the plurality of the channels, and the second branch channel assembly being connected between each separate port and the second end of each said channel, the fluid injected into the channels is smooth and uniform.

In one embodiment of the present application, as shown in FIGS. 1-2, the first branch channel assembly 4 comprises a plurality of stages of branch channels. Each said stage comprises at least one junction 411, 421, 431, 441, 451, and at least two branch channels 412, 422, 432, 442, 452 diverged from each of the at least one junction. A free end of each said branch channel 412, 422, 432, 442, 452 of each said stage of the first branch channel assembly 4 form a junction 421, 431, 441, 451 of a next stage. The synchronized port 1 is in connection with or serves as a primary junction 411 at a primary stage of the first branch channel assembly 4, free ends of branch channels 452 at a final stage of the first branch channel assembly 4 are in direct connection with the first ends of the plurality of the channels 3. In one embodiment of the present application, for each said stage in the first branch channel assembly 4, the number of the branch channels 412, 422, 432, 442, 452 diverged from each of the at least one junction is two. The two branch channels 412, 422, 432, 442, 452 are symmetrically diverged from each of the at least one junction 411, 421, 431, 441, 451 relative to a length direction of each said channel 3. The first branch channel assembly 4 is configured to be symmetric relative to a line passing through the primary junction 411 thereof in the length direction of each said channel 3.

A schematic structural diagram of the first branch channel assembly 4 in accordance with one embodiment of the present application is shown in FIG. 2. For a primary stage of branch channels in the first branch channel assembly 4, the synchronized port 1 may be directly used as a primary junction 411 of the first branch channel assembly 4 from which two primary branch channels 412 are diverged. In other embodiments, the synchronized port 1 may also be in connection with the primary junction 411. Free ends of the primary branch channels 412 form secondary junctions 421 of a secondary stage, and secondary branch channels 422 are diverged from each secondary junction 421. Free ends of the secondary branch channels 422 form tertiary junctions 431 of a tertiary stage, and tertiary branch channels 432 are diverged from each tertiary junctions 431. A quaternary stage comprising quaternary junctions 441 and quaternary branch channels 442 diverged therefrom, and a quinary stage comprising quinary junctions 451 and quinary branch channels 452 are configured in the similar way. The free ends of the quinary branch channels 452 are in direct connection with the first ends of the plurality of the channels 3.

Preferably, for each stage of branch channels of the first branch channel assembly 4, two branch channels 412, 422, 432, 442, 452 are symmetrically diverged from each junction 411, 421, 431, 441, 451 of said stage relative to a length direction of the channel 3, which means that with the diverged angles relative to the length direction, the widths and the lengths of at least two branch channels diverged from the same junction are the same, and the arrangement of the at least two branch channels diverged from the same junction are symmetric relative to the length direction of the channel 3.

The number of the free ends of a final stage of the first branch channel assembly 4 is not limited to eight as indicated in FIGS. 1-2, it may be two, four, eight, or even more with the adjustment of the number of the stages of the first branch channel assembly 4, and preferably, the number of the free ends of the final stage of each second branch channel assembly 5 is four or eight.

Preferably, the first branch channel assembly 4 is configured to be symmetric relative to a line passing through the primary junction 411 thereof in the length direction of each said channel 3. In this way, when the synchronized mode is used to introduce the same sample or reagent to the plurality of the channels 3, different flow path of the fluid may reach the plurality of the channels 3 at the same time, and the flow pattern of the fluid into the plurality of the channels 3 is smooth and uniform.

In one embodiment of the present application, as shown in FIGS. 1 and 3, each said second branch assembly 5 comprises a plurality of stages of branch channels. Each said stage comprises at least one junction 511, 521, 531, and at least two branch channels 512, 522, 532 diverged from each of the at least one junction. A free end of each said branch channel 512, 522, 532 of each said stage of each said second branch assembly 5 form a junction 521, 531 of a next stage. Each said separate port 2 is in connection with or serves as a primary junction 511 at a primary stage of each said second branch assembly 5, and free ends of branch channels 532 at a final stage of each said second branch assembly 5 are in direct connection with the second end of each said channel 3. Each said second branch assembly 5 is configured to be symmetric relative to a line passing through the primary junction 511 thereof in the length direction of each said channel 3. In one embodiment of the present application, for each said stage in each said second branch assembly 5, the number of the branch channels diverged from each of the at least one junction is two. The two branch channels 512, 522, 532 are symmetrically diverged from each of the at least one junction 511, 521, 531 relative to a length direction of each said channel 3; and each said second branch assembly 5 is configured to be symmetric relative to a line passing through the primary junction thereof in the length direction of each said channel 3.

A schematic structural diagram of the first branch channel assembly in accordance with one embodiment of the present application is shown in FIG. 3. For a primary stage of branch channels in each second branch channel assembly 5, a corresponding separate port 2 may be in connection with the primary junction 511 of the second branch channel assembly 5 from which two primary branch channels 512 are diverged. In other embodiments, the separate port 2 may also be directly used as a primary junction 511. Free ends of the primary branch channels 512 form secondary junctions 521 of a secondary stage, and secondary branch channels 522 are diverged from each secondary junction 521. Free ends of the secondary branch channels 522 form tertiary junctions 531 of a tertiary stage, and tertiary branch channels 532 are diverged from each tertiary junctions 531. Free ends of the tertiary branch channels 532 are in direct connection with the second ends of the plurality of the channels 3.

Preferably, for each stage of branch channels of the second branch channel assembly 5, the two branch channels 512, 522, 532 are symmetrically diverged from each junction 511, 521, 531 of said stage relative to the length direction of the channel 3, which means that with the bifurcation angles relative to the length direction, the widths and the lengths of two branch channels 512, 522, 532 diverged from the same junction are the same, and the arrangement of the at least two branch channels diverged from the same junction are symmetric relative to the length direction of the channel 3.

The number of the free ends of a final stage of each second branch channel assembly 5 is not limited to eight as indicated in FIGS. 1 and 3, it may be two, four, eight, or even more with the adjustment of the number of the stages of the second branch channel assembly 5, and preferably, the number of the free ends of the final stage of each second branch channel assembly 5 is four or eight.

Preferably, each said second branch assembly 5 is configured to be symmetric relative to a line passing through the primary junction 511 thereof in the length direction of each said channel 3. In this way, when the independent mode is adopted to simultaneously introduce different samples or reagents into the plurality of the channels 3 respectively, the samples or reagents introduced into each channel 3 from each separate port 2 is uniformly distributed.

In one embodiment of the present application, the number of the stages of the plurality of the second branch channel assemblies 5 are equivalent, such that the different samples or reagents simultaneously introduced into the second branch channel assemblies 5 via the separate ports 2 can reach the plurality of the channels 3 at the same time, and the processing durations for different procedures in the plurality of the channels 3 can be equivalent under the control of a flow path control system.

In one embodiment of the present application, for each of the plurality of the channels 3, the number of the branch channels 452 in direct connection with the first end is equivalent to the number of the branch channels 532 in direct connection with the second end, such that a smooth and uniform flow pattern can be obtained.

In one embodiment of the present application, the plurality of the channels 3 have the same structures, and the plurality of the channels 3 are symmetrically arranged relative to a line passing through the primary junction 411 of the first branch channel assembly 4 in the length direction of each said channel 3.

In one embodiment of the present application, the substrate is made of a material comprising a rubber, a resin, a polycarbonate (PC), a polydimethylsiloxane (PDMS), or a polymethylmethacrylate (PMMA).

Figure 4:
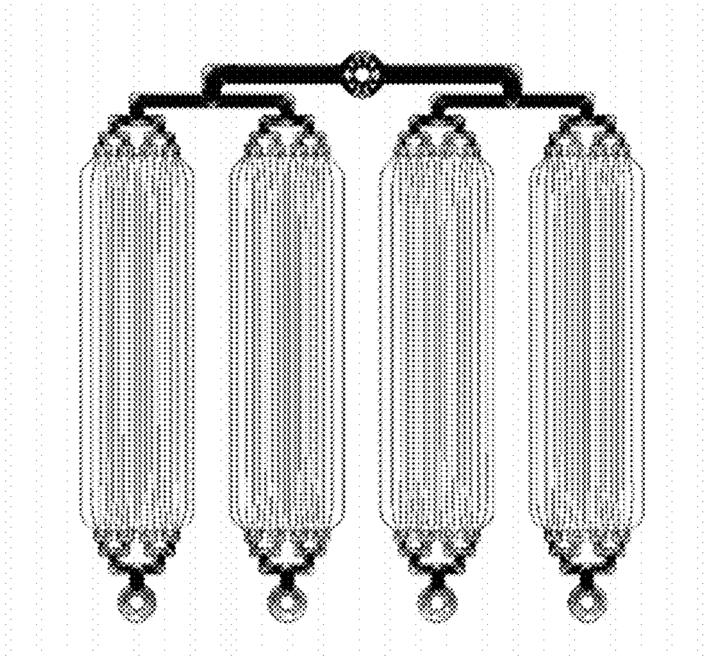
FIG. 4 illustrates a streamline profile of the multi-channel microfluidic device for multi-parallel analyte detection according to an embodiment of the present application.
Figure 5A:
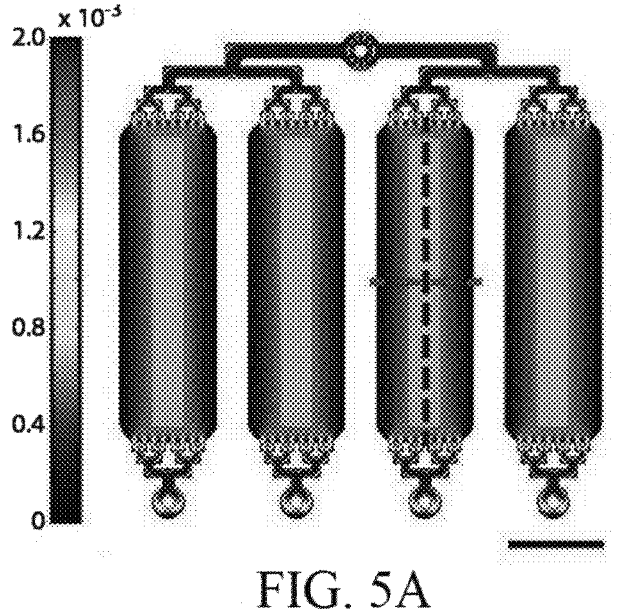
FIGS. 5A, 5B, and 5C illustrates a fluidic field of the multi-channel microfluidic device simulated by COMSOL according to an embodiment of the present application.
Figure 5B:
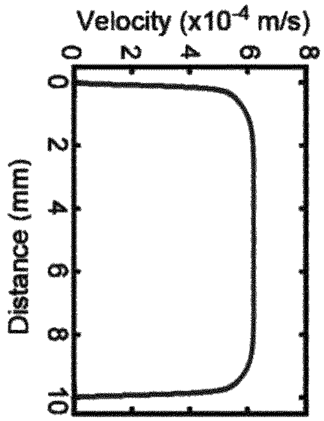
Figure 5C:
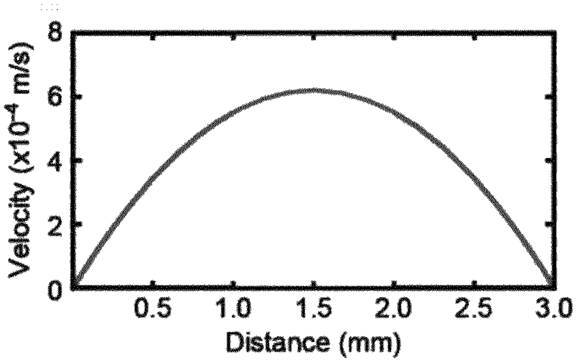

Example 2 Demonstration of the Flow Pattern of the Multi-Channel Microfluidic Device A multi-channel microfluidic device according to the Example 1 is provided. The microfluidic device has four channels, a detection region of each channel has a length of 10 mm, a width of 3 mm, and a height of 10 micrometer (m), such a device only requires 3 μL of the sample or reagent. FIG. 4 shows the streamline profile of the four-channel microfluidic device, which indicates a smooth and uniform flow pattern by the assistance of the first branch channel assembly and the second branch channel assemblies at the two ends of multi-channel microfluidic device. In addition, the smooth and uniform flow pattern along different channels was further confirmed by using a finite element simulation software COMSOL® to simulate the fluid field pattern of a multi-channel microfluidic device, results of which are shown in FIGS. 5A-5C, and the flow velocity versus the distance along the length direction and the flow velocity versus the distance along the width direction are respectively shown in FIGS. 5B-5C. As shown in FIGS. 5A-5C, the flow velocity pattern is almost identical among the four channels. The length and the width of the region with 10% velocity variance is 8.5 mm×1 mm, which is sufficient for multi-point analyte detection. Specifically, FIG. 5A shows fluidic field effects in the plurality of the channels simulated by COMSOL, the microfluidic device has four channels, a detection region of each channel has a length of 10 millimeter (mm), a width of 3 mm, and a height of 10 micrometer (m), and only 3 microliter (μL) of the sample or reagent is required; FIG. 5B shows the flow velocity versus the distance along the length direction, in which, flow velocity within 10% of a maximum velocity is represented by a shaded region; and FIG. 5C shows the flow velocity versus the distance along the width direction, in which, flow velocity within 10 percent (%) of a maximum velocity is represented by a shaded region. Scale bar is 3 mm.

Figure 6:
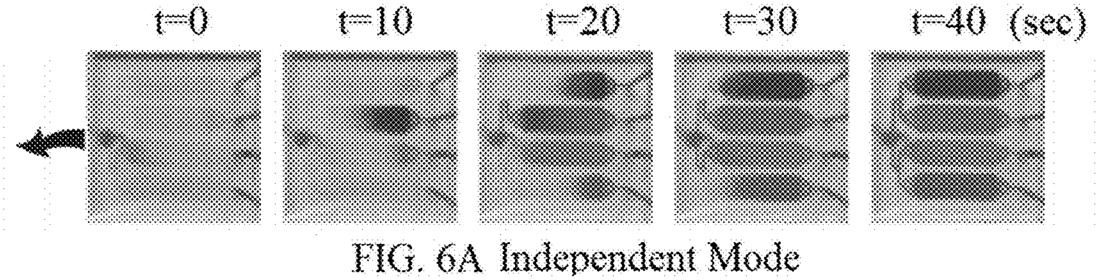
FIGS. 6A, 6B, and 6C are pictures illustrating a food dye demonstration of the dual-mode microchannel under different modes of operation according to an embodiment of the present application.
Figure 6:
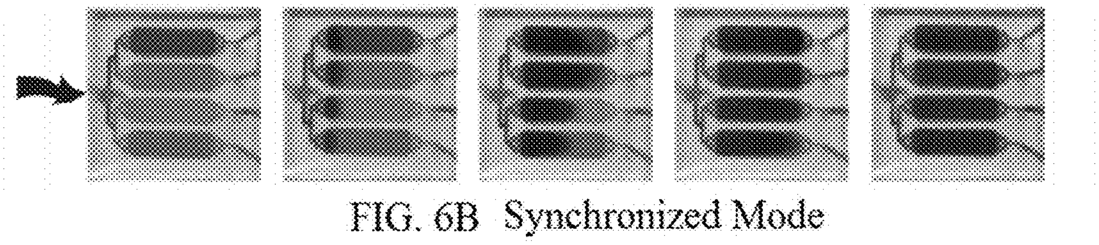
Figure 6:
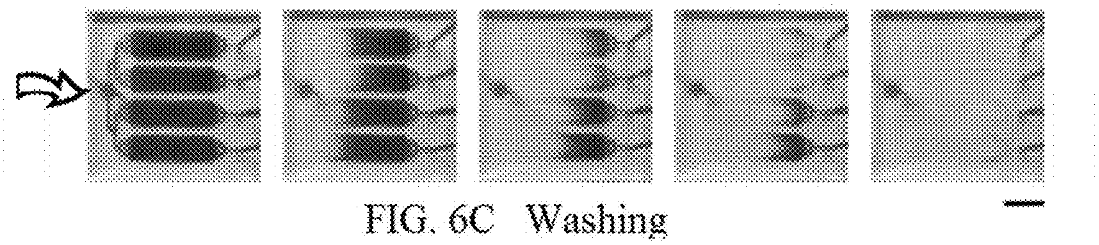

A food dyes experiment was also conducted to confirm the flow pattern of the multi-channel device. In the independent mode, four different food dies were injected into the four channels respectively via the separate ports, pictures were taken at the following time points: t=0, 10, 20, 30, and 40 seconds, as shown in FIG. 6A. Thereafter, a fifth food dye was injected into the four channels via the synchronized port, pictures were taken at the following time points: t=0, 10, 20, 30, and 40 seconds, as shown in FIG. 6B. Finally, a solution was injected into the four channels via the synchronized port to wash the dies in the channels, pictures were also taken at the following time points: t=0, 10, 20, 30, and 40 seconds, as shown in FIG. 6C. Results in FIGS. 6A-6C agree with the simulation results, and the flow patterns in the channels are smooth and uniform. Scale bar: 5 mm. FIG. 6A shows the injection of four different food dies via the separate ports in the independent mode, FIG. 6B shows the injection of a fifth food dye via the synchronized port in the synchronized mode, and FIG. 6C shows injection of a Phosphate-buffered saline (PBS) solution via the synchronized port in the synchronized mode to wash the food dies in the channels.

Example 3 Method of Using the Multi-Channel Microfluidic Device

In another aspect of the present application, there is provided a method for using the above-described multi-channel microfluidic device in Example 1. The method comprises:

a) using the synchronized port 1 as an inlet when the plurality of the channels are to be performed with identical parallel procedures; and b) using at least a part of the separate ports 2 as separate inlets when at least a part of the plurality of the channels are to be simultaneously performed with independent procedures.

In one embodiment, the multi-channel microfluidic device is controlled by a channel control system.

In practical use, the multi-channel microfluidic device can be integrated with different sensor schemes, such as nanoplasmonic or electric-based sensors, and a biological sensitive recognition element (such as antibodies, nucleic acids, enzymes, or aptamers) can be immobilized on the microfluidic device to identify the presence of one or more specific analytes.

Herein, an experiment using the Anti-Mouse IgG as the biological recognition element to detect Mouse IgG antigen was conducted to testify the use of the multi-channel microfluidic device as described in Example 1. The multi-channel microfluidic device was integrated with a nanoplasmonic sensor to perform the real-time IgG detection. FIGS. 7A-7D illustrate experiment procedures including the localized surface plasmon resonance (LSPR) sensor surface functionalization and immunoassay protocol and the automatic microfluidic system workflow for the experiment protocol according to an embodiment of the present application.

As shown in FIGS. 7A-7D, a microfluidic system is constructed, of which, the multi-channel microfluidic device (2 cm×2 cm) consists of four independent channels, each with a large detection region (L: 10 mm; W: 3 mm; H: 100 μm) and only requires 3 μL of sample, other microfluidic components may be provided by LabSmith. The whole system (18 centimeter (cm)×26 cm) comprised an 80 μL micropump and eight microvalves controlled by a customized program. R1-R12 in the FIGS. 7A-7D indicate reagent pools, of which, R1 is added with 11-Mercaptoundecanoic acid (MUA), R2 is added with a mixture of 1-Ethyl-3-(3-dimethylaminopropyl)-carbodiimide (EDC) and N-hydroxysuccinimide (NHS), R3 is added with antigen, R4 is added with a phosphate buffer saline (PBS), R5 is added with ethanol, and R6 is added with a mixture of ethanol and, R7 and R12 are configured to receive waste, and R8-R11 are added with antibodies of different concentrations. All samples and buffers were sequentially flowed into a dual-mode polydimethylsiloxane (PDMS) microchannel as described in Example 1.

Depending on the different flow direction, two operation modes were adopted: on one hand, when identical procedures were required for all the channels, the synchronized mode was employed; on the other hand, when parallel, independent processes were required, the independent mode was employed. To switch between different modes, it only required to exchange the input(s) and output(s) of the network between the ports, this was realized by the periphery channel control system and the customized program.

Figures 7A, 7B, 7C, 7D:
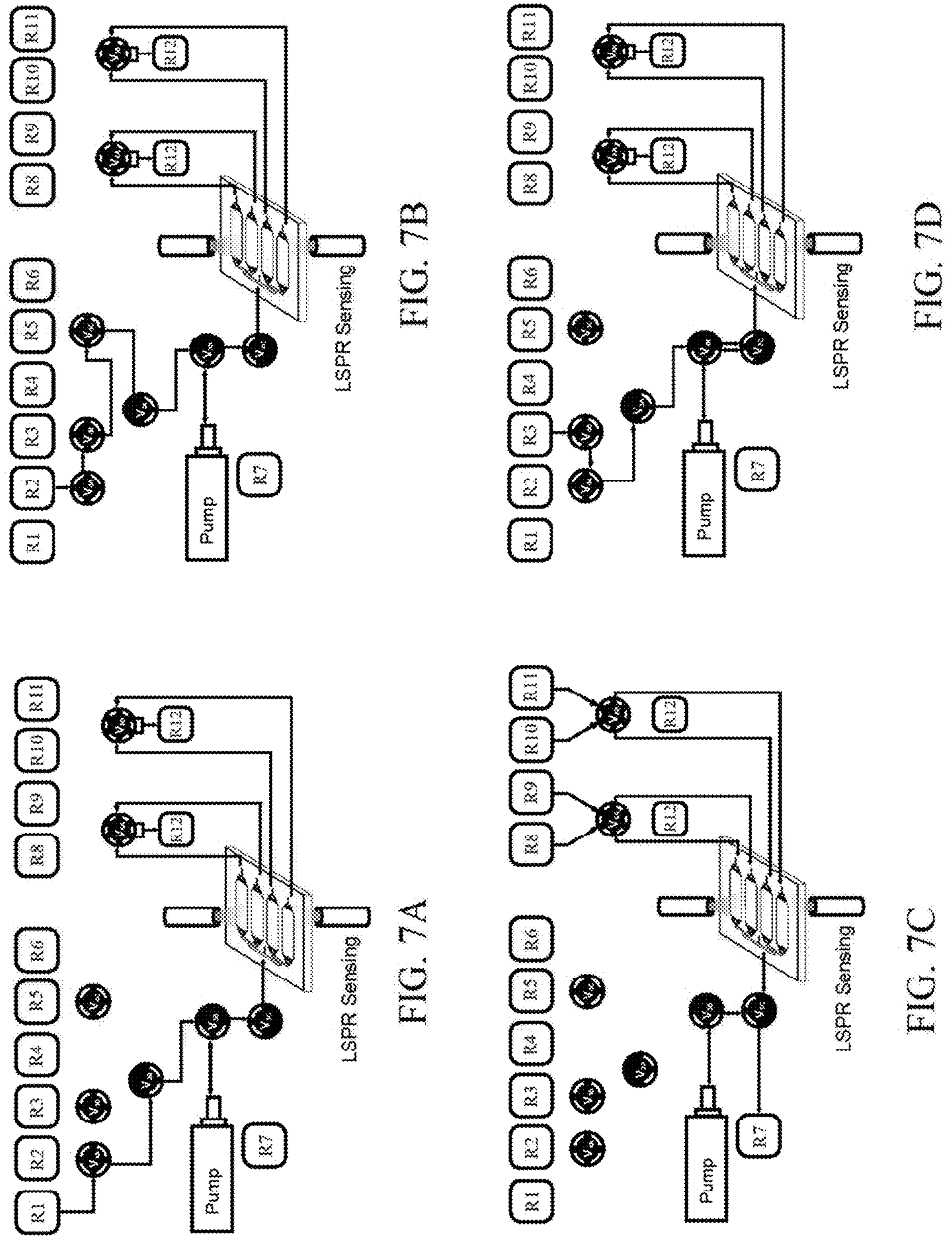
FIGS. 7A, 7B, 7C, and 7D illustrate experiment procedures including the localized surface plasmon resonance (LSPR) sensor surface functionalization and immunoassay protocol and the automatic microfluidic system workflow for the experiment protocol according to an embodiment of the present application.

As shown in FIGS. 7A-7D, the detailed operational procedure is as follows:

1) Functionalization of sensor with MUA shown in FIG. 7A;

2) Activation of the surface with a mixture of EDC and NHS shown in FIG. 7B;

3) Immobilization of antibody shown in FIG. 7C; and

4) Detection of sample shown in FIG. 7D.

The workflow for immobilization and detection can be exchanged depending on the type of experiment.

It should be understood that in order to clearly show the flow path control in different operation steps, arrow lines in FIGS. 7A-7D are used to indicate the direction of the flow path in different operation steps, which by no means indicates that other components not connected by arrow lines are not in connection. It should be noted that after the functionalization operation, the multi-channel microfluidic device is washed by ethanol, the mixture of ethanol and the PBS, and the PBS, respectively, and after each of operations of the activation of the surface, immobilization of the antibodies, and the sample detection, the multi-channel microfluidic device is washed by the PBS. The functionalization and activation of the sensor was operated in the synchronized mode to achieve uniform sensor preparation among the four channels. Next, to achieve multiplexing, four different types of antibodies were loaded into the network under the independent mode during the immobilization step. Finally, the sample was loaded into the network under the synchronized mode for simultaneous detection of multiple analytes in the sample. The washing operations of the multi-channel microfluidic device were also operated in the synchronized mode.

Figure 8A:
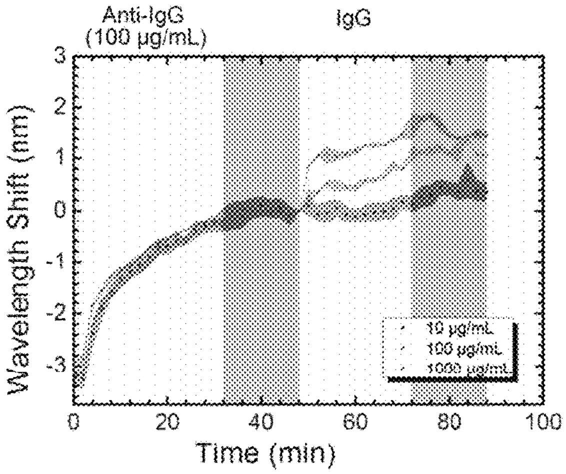
FIGS. 8A and 8B shows the detection of the Immunoglobulin G (IgG) using the anti-IgG according to an embodiment of the present application.
Figure 8B:
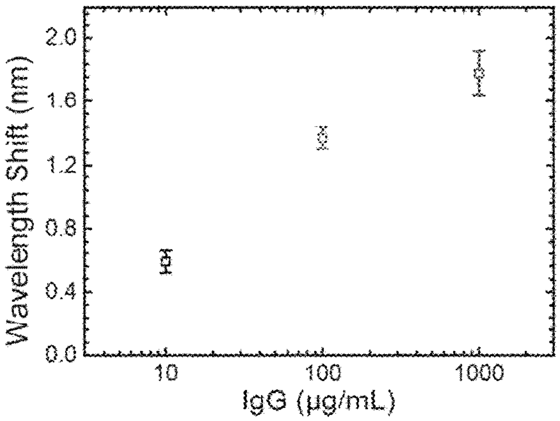

FIGS. 8A-8B shows the detection of the Immunoglobulin G (IgG) using the anti-IgG according to an embodiment of the present application. Specifically, FIG. 8A is the average (dots) and standard deviation (shaded regions around the doted lines) of the binding of anti-IgG and the multi-parallel detection of IgG (n=4 in each channel), in which, shaded rectangular regions represent the PBS washing. FIG. 8B is the peak wavelength shift corresponding to different IgG concentrations (n=10). FIG. 8A shows the real-time immunoglobulin binding event of 100 microgram/milliliter (μg/mL) Anti-Mouse IgG (synchronized mode) and serial dilutions of Mouse IgG antigen (independent mode) introduced simultaneously into different channels. In addition, at the end of each PBS washing step, the absorbance spectra are measured to compare the peak wavelength shift (FIG. 8B). Based on the results, it is demonstrated that the LSPR sensor integrated with the dual-mode microchannel operated by the automatic microfluidic system has the ability to achieve multi-parallel detection in separate channels simultaneously.

To summarize, the multi-channel microfluidic device can potentially be integrated with various sensors, which can achieve real-time, multiplex, and sample-efficient analyte detection capabilities in point-of-care approaches.

The terms “comprising,” “having,” “including,” and “containing” are to be construed as open-ended terms (i.e., meaning “including, but not limited to,”) unless otherwise noted. While particular embodiments of the disclosure have been shown and described, it will be obvious to those skilled in the art that changes and modifications may be made without departing from the disclosure in its broader aspects, and therefore, the aim in the appended claims is to cover all such changes and modifications as fall within the true spirit and scope of the disclosure.

What is claimed is:

1. A multi-channel microfluidic device for multi-parallel analyte detection, comprising:

a substrate; and a multi-channel microfluidic assembly formed in the substrate, the multi-channel microfluidic assembly comprising:

a synchronized port;

a plurality of separate ports;

a plurality of channels arranged in parallel, each channel of the channels having a first end and a second end opposite to the first end;

a first branch channel assembly; and a plurality of second branch assemblies, the synchronized port being coupled with all of the first ends of the channels via the first branch channel assembly, and each of the separate ports being coupled with the second end of each of the channels via each second branch assembly.

2. The multi-channel microfluidic device of claim 1, wherein the first branch channel assembly comprises a plurality of stages of branch channels, each stage of the stages of branch channels comprising:

at least one junction; and at least two branch channels diverged from each junction of the at least one junction;

a free end of each branch channel of the each stage of the stages of branch channels of the first branch channel assembly form a junction of a next stage, the synchronized port is coupled with or serve as a primary junction at a primary stage of the first branch channel assembly, and free ends of branch channels at a final stage of the first branch channel assembly are in direct connection with the first ends of the channels.

3. The multi-channel microfluidic device of claim 2, wherein for the each stage of the stages of branch channels in the first branch channel assembly, a number of the branch channels diverged from each junction of the at least one junction is two, the two branch channels are symmetrically diverged from each junction of the at least one junction relative to a length direction of each of the channels, and the first branch channel assembly is configured to be symmetric relative to a line passing through the primary junction thereof in the length direction of the each channel.

4. The multi-channel microfluidic device of claim 2, wherein each second branch assembly comprises a plurality of stages of branch channels, each stage of the stages of branch channels of the each second branch assembly comprising:

at least one junction, and at least two branch channels diverged from each of the at least one junction;

a free end of each branch channel of the each stage of branch channels of the each second branch assembly form a junction of a next stage; and each separate port is in connection with or serve as a primary junction at a primary stage of the each second branch assembly, and free ends of branch channels at a final stage of the each second branch assembly are in direct connection with the second end of the each channel.

5. The multi-channel microfluidic device of claim 4, wherein for the each stage in the each second branch assembly, a number of the branch channels diverged from each junction of the at least one junction is two, the two branch channels are symmetrically diverged from each junction of the at least one junction relative to a length direction of each of the branch channels, and each second branch assembly is configured to be symmetric relative to a line passing through the primary junction thereof in the length direction of the each channel.

6. The multi-channel microfluidic device of claim 4, wherein for each of the channels, a number of the branch channels directly connected with the first end is equivalent to the number of the branch channels directly connected with the second end.

7. The multi-channel microfluidic device of claim 5, wherein the channels have the same structures, and the plurality of the channels are symmetrically arranged relative to a line passing through the primary junction of the first branch channel assembly in the length direction of the each channel.

8. The multi-channel microfluidic device of claim 1, wherein the device is configured to immobilize a biological sensitive recognition element, and configured to be integrated with a sensor to identify one or more analytes.

9. A method for multi-parallel analyte detection, comprising:

- providing a multi-channel microfluidic device, comprising a substrate and a multi-channel microfluidic assembly formed in the substrate, the multi-channel microfluidic assembly comprising:
  - a synchronized port;
  - a plurality of separate ports;
  - a plurality of channels arranged in parallel, each channel of the channels having a first end and a second end opposite to the first end;
  - a first branch channel assembly; and
  - a plurality of second branch assemblies, the synchronized port being coupled with all of the first ends of the channels via the first branch channel assembly, and each of the separate ports being coupled with the second end of each of the channels via each of second branch assembly;
- using the synchronized port as an inlet when the channels are to be performed with identical parallel procedures; and
- using at least a part of the separate ports as separate inlets when at least a part of the channels are to be simultaneously performed with independent procedures.

10. The method of claim 9, further comprising controlling the multi-channel microfluidic device by a channel control system.

11. The method of claim 9, further comprising using the multi-channel microfluidic device to immobilize a biological sensitive recognition element and to identify one or more specific analytes when integrated with a sensor.

12. The method of claim 9, wherein the first branch channel assembly comprises a plurality of stages of branch channels, each stage of branch channel comprising:

- at least one junction and at least two branch channels diverged from each of the at least one junction; and
- a free end of each branch channel of the each stage of branch channel of the first branch channel assembly form a junction of a next stage, the synchronized port is coupled with or serve as a primary junction at a primary stage of the first branch channel assembly, and free ends of branch channels at a final stage of the first branch channel assembly are in direct connection with the first ends of the channels.

13. The method of claim 12, wherein for the each stage of branch channels in the first branch channel assembly, a number of the branch channels diverged from each junction of the at least one junction is two, the two branch channels are symmetrically diverged from each of the at least one junction relative to a length direction of each of the channels, and the first branch channel assembly being configured to be symmetric relative to a line passing through the primary junction thereof in the length direction of the each channel.

14. The method of claim 12, wherein each second branch assembly comprises a plurality of stages of branch channels, each stage of branch channels of the stages of the each second branch assembly comprising:

- at least one junction and at least two branch channels diverged from each of the at least one junction; and
- a free end of each branch channel of the each stage of branch channels of the each second branch assembly form a junction of a next stage, and each separate port of the plurality of separate ports is coupled with or serve as a primary junction at a primary stage of each of the second branch assemblies, and free ends of branch channels at a final stage of each of the second branch assemblies are in direct connection with the second end of the each channel.

15. The method of claim 14, wherein for the each stage in the each second branch assembly, a number of the branch channels diverged from each junction of the at least one junction is two, the two branch channels are symmetrically diverged from each junction of the at least one junction relative to a length direction of each of the channels, and the each second branch assembly being configured to be symmetric relative to a line passing through the primary junction thereof in the length direction of the each channel.

16. The method of claim 14, wherein for each of the channels, a number of the branch channels directly connected with the first end is equivalent to the number of the branch channels directly connected with the second end.

17. The method of claim 15, wherein the channels have the same structures, and the channels are symmetrically arranged relative to a line passing through the primary junction of the first branch channel assembly in the length direction of the each channel.

18. The microfluidic system for multi-parallel analyte detection, comprising:

- a multi-channel microfluidic device, comprising:
  - a substrate; and
  - a multi-channel microfluidic assembly formed in the substrate, the multi-channel microfluidic assembly comprising:
    - a synchronized port;
    - a plurality of separate ports;
    - a plurality of channels arranged in parallel, each channel of the channels having a first end and a second end opposite to the first end;
    - a first branch channel assembly; and
    - a plurality of second branch assemblies, the synchronized port being coupled with all of the first ends of the channels via the first branch channel assembly, and each of the separate ports being coupled with the second end of each of the channels via each second branch assembly.

* * * * *